United States Patent [19]
Alftine

[11] 4,442,698
[45] Apr. 17, 1984

[54] MOLECULAR SIEVE OXYGEN MONITOR

[75] Inventor: David N. Alftine, Bettendorf, Iowa

[73] Assignee: Litton Systems, Inc., Davenport, Iowa

[21] Appl. No.: 460,307

[22] Filed: Jan. 24, 1983

[51] Int. Cl.³ .............................................. G01N 31/06
[52] U.S. Cl. ........................................................ 73/23
[58] Field of Search ........................ 73/23; 137/624.14

[56] References Cited
U.S. PATENT DOCUMENTS

| | | | |
|---|---|---|---|
| 2,760,511 | 8/1956 | Greeff | 137/624.14 X |
| 3,151,623 | 10/1964 | Riordan | 137/624.14 X |
| 4,205,700 | 6/1980 | Bouteille | 137/624.14 X |

Primary Examiner—Gerald Goldberg
Assistant Examiner—Vince Kovalick
Attorney, Agent, or Firm—Brian L. Ribando

[57] ABSTRACT

A monitoring system for determining the concentration of oxygen in the product gas of an oxygen enriching system comprises a plurality of pneumatic nor gates. Means are provided for coupling the outlet port of each gate to the control port of the subsequent gate to form a closed loop and a plurality of molecular sieve beds are pneumatically connected one each to the control port of the nor gates. The molecular sieve beds adsorb oxygen from the product gas to attenuate the rate of pressure change in the control ports and thus, the oscillation frequency of the monitor. The oxygen concentration of the product gas may be inferred from the oscillation frequency of the monitor.

3 Claims, 2 Drawing Figures

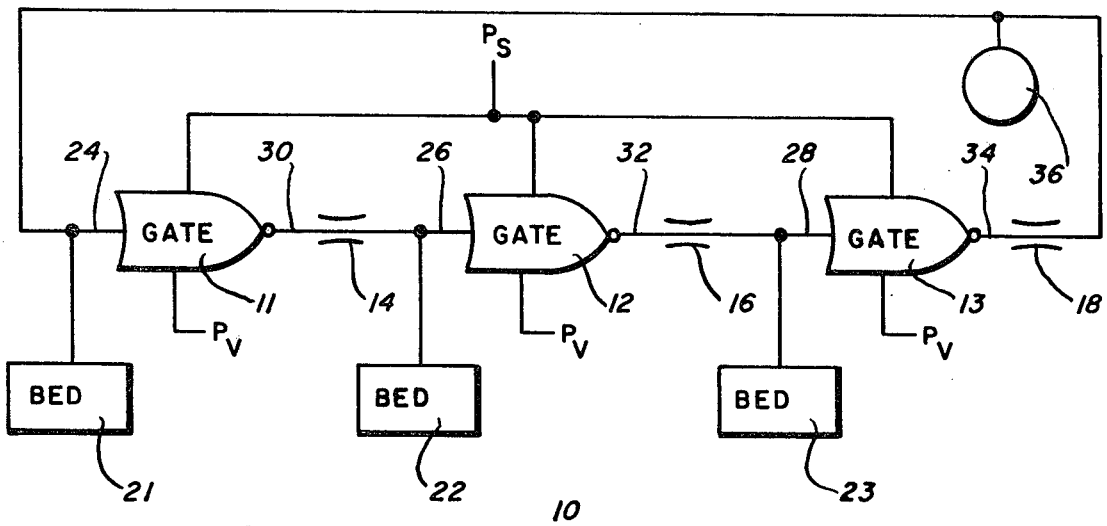
Fig_1
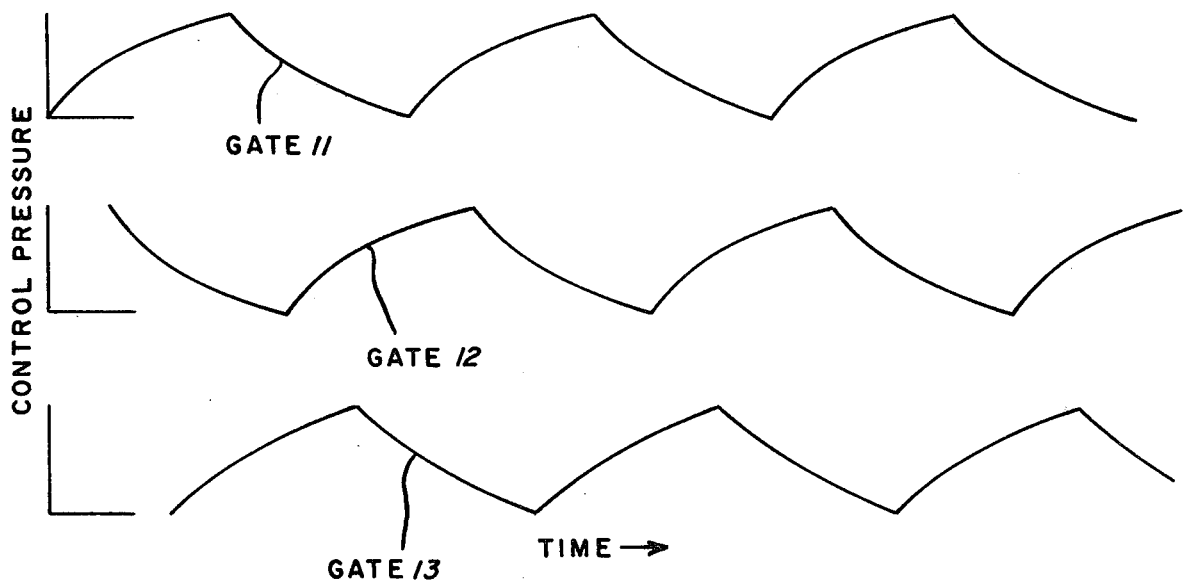
Fig_2

MOLECULAR SIEVE OXYGEN MONITOR

BACKGROUND OF THE INVENTION

Oxygen enriched breathing systems such as are found in hospitals and aircraft use as oxygen sources bottled high pressure gas, liquid oxygen, solid oxygen generators, commonly referred to as "candles", or fractionalized air. It can become critical that the user know the oxygen concentration in the breathing system to avoid a catastrophic event such as could occur in high alitude aircraft.

Air fractionalizing is normally accomplished by alternating the flow of high pressure air through each of two beds of molecular sieve material such as a zeolite. This process is identified as the pressure swing adsorption technique. Systems employing this technique can be made to produce either a nitrogen or an oxygen enriched effluent based on the type of zeolite chosen. Some zeolites adsorb oxygen and others nitrogen. In an oxygen enriching system, a zeolite which adsorbs nitrogen would be selected.

These same adsorption characteristics of a zeolite can be used in monitoring the effluent concentrations of product gas from an air fractionalizing system or any other source.

SUMMARY AND OBJECTS OF THE INVENTION

According to the invention, a molecular sieve oxygen monitor is used to determine the oxygen concentration of the product gas of an oxygen enriching system through the application of a plurality of beds of molecular sieve material such as a zeolite to adsorb oxygen from samples of the system effluent.

Though the description of the monitor focuses principally on oxygen enriching systems, it is understood that the monitor applies equally to nitrogen enriching systems or any other enriched product gas for which a suitable adsorber exists.

It is therefore an object of this invention to provide a monitor for determining the oxygen concentration of the product gas of an oxygen enriching system.

It is another object of this invention to provide a monitor which continuously samples the product gas to monitor oxygen concentration.

BRIEF DESCRIPTION OF THE DRAWINGS

FIG. 1 is a schematic representation of a molecular sieve oxygen monitor according to the invention.

FIG. 2 is a pressure swing profile of the molecular sieve oxygen monitor of FIG. 1 illustrating the control line pressure excursions of the pneumatic nor gate circuits comprising the monitor.

DETAILED DESCRIPTION OF THE PREFERRED EMBODIMENT

Referring to FIG. 1, a molecular sieve oxygen monitor 10 is a pneumatic oscillator which includes a plurality of nor gates 11, 12, and 13 interconnected such that the output of each gate is the control of a subsequent gate in a closed loop series. The output of the gate 11 is connected to the control of the gate 12 as the output of the gate 11 passes through a restrictive orifice 14, the output of the gate 12 is connected to the control of the gate 13 passing through a restrictive orifice 16, and the output of the gate 13 is connected to the control of the gate 11 passing through a restrictive orifice 18. In parallel with each of the gate controls are beds 21, 22, and 23 of molecular sieve material such as a zeolite which adsorb oxygen. Effluent gas samples $P_s$ from an oxygen enriching supply (not shown) are continuously provided to each of the gates 11, 12, and 13. The effluent gas $P_s$ flows through each of the gates 11, 12, and 13 when the gate control pressure is reduced to a preset lower limit allowing the gate to open. Conversely, the flow of effluent gas is blocked when the control pressure reaches a preset upper limit and the gate closes. The rise and decay rate of the control pressure is a function of the oxygen concentration of the effluent gas samples $P_s$. Pressure decay takes place when the gate output is allowed to vent to the atmosphere through vent ports $P_v$.

MODE OF OPERATION OF THE PREFERRED EMBODIMENT

The pneumatic nor gates 11, 12, and 13 function in response to control pressure levels. When the control pressure in lines 24, 26, or 28 is at a predetermined low level, the output pressure of the respective gate in lines 30, 32, or 34 is at the pressure of the sample gas $P_s$ and the gate is said to be open. Conversely, when the pressure in the control lines 24, 26, or 28 reaches a predetermined high pressure, the output of the respective gate in the lines 30, 32, or 34 is dropped to the pressure at the vent ports $P_v$ and the gate is said to be closed.

The beds 21, 22, and 23 of molecular sieve material adsorb oxygen from the sample gas $P_s$ when the respective gate 11, 12, or 13 is open. The beds 21, 22, and 23 desorb oxygen when the respective gate 21, 22, or 23 is closed and the lines 30, 32, and 34 are at pressure at the vent ports $P_v$. The adsorption and desorption of oxygen by the molecular sieve beds 21, 22, and 23 inhibits the rate of pressure rise and decay in the control pressure in lines 24, 26, and 28 in a direct proportion to the concentration of oxygen in the effluent gas samples $P_s$. FIG. 2 illustrates the pressure rise and decay profile of the control pressure at lines 24, 26, and 28 as the gates 11, 12 and 13 open and close.

In addition to the pressure rise and decay rate restriction created by the molecular sieve beds 21, 22, and 23, restrictive orifices 14, 16, and 18 also inhibit the rate of pressure rise and decay. The molecular sieve monitor 10 is a pneumatic oscillator whose frequency of oscillation is a function of the time required for the control pressure to reach its predetermined high and low pressure levels to close and open the gates 11, 12, and 13. Should the molecular sieve beds 21, 22, and 23 not inhibit the rate of pressure rise and decay, such as would occur when the sample gas $P_s$ was nitrogen rich, the restrictive orifices 14, 16, and 18 introduce a time delay in the pressure rise and decay to establish a set maximum oscillation frequency.

The monitor 10 is activated when the sample gas $P_s$ pressure is applied to the gates 11, 12, and 13. With no control pressure in the lines 24, 26, and 28, the gates are all open and sample gas $P_s$ pressure appears at the gate output lines 30, 32, and 34. The pressure in the control lines 24, 26, and 28 rises as a function of the flow through the restrictive orifices 14, 16, and 18 which flow is a function of the pressure of the sample gas $P_s$. The rate of pressure rise in the control lines is further inhibited by the adsorption of oxygen from the sample gas $P_s$ in the molecular sieve beds 21, 22, and 23. Due to slight differences in the size and adsorptive rates of each of the sieve beds 21, 22, and 23, each control line 24, 26, and 28 reaches the predetermined pressure level at which it closes its gate at a different point in time. When any one gate closes first, its output line vents through its port $P_v$ holding the subsequent gate open. When the control pressure in the remaining gate reaches the predetermined level at which it closes, its output pressure vents through its port $P_v$ causing the control pressure of the gate first closed to decay, reopening the first gate, closing the second gate, opening the third, closing the first and so on.

The rate of pressure rise and decay of each of the control lines varies as a function of the amount of oxygen adsorbed from the sample gas $P_s$ by the sieve beds 21, 22, and 23, and the frequency of the gates opening and closing is a function of the rate of pressure rise and decay. The oxygen content of the sample gas $P_s$ can be inferred as the oscillation frequency decreases as oxygen content increases. The level of the oxygen concentration of the sample gas $P_s$ can be inferred if an oscillation frequency for the monitor 10 is first determined for a given level of nitrogen enrichment and for a given level of oxygen enrichment. The oscillation frequency is read and displayed by a suitable counter 36.

It is clear that this molecular sieve adsorptive technique is equally applicable to any enriched product gas for which an adsorber is available for the enriching component of that gas.

What is claimed is:

1. A monitoring system for determining the concentration of oxygen in the product gas of an oxygen enriching system comprising:

a plurality of pneumatic nor gates coupled in series to form a closed loop each nor gate in a first open condition, directing the flow of said product gas to an outlet port of said gate and, in a second closed condition, blocking the flow of said product gas and coupling the outlet port of said gate to a vent port of said gate, means for coupling the outlet port of each gate to the control port of the subsequent gate to form said closed loop thereby causing the gates to sequentially open and close such that each subsequent gate assumes an open or closed condition opposite to the condition of the preceding gate, the pneumatic pressure means at said outlet port for causing the subsequent gate to go to either an open or closed condition, a corresponding plurality of molecular sieve beds each pneumatically connected to the control port of said nor gates to adsorb oxygen from said product gas, in said first open condition attenuate the rate of pressure rise in said control ports, and in said second closed condition attenuate the rate of pressure decay in said control port, and means for inferring the oxygen concentration of said product gas from the oscillation frequency of the monitor.

2. A monitoring system for determining the concentration of any particular gas in a system for producing a product gas enriched in that particular gas comprising:

a plurality of pneumatic nor gates coupled in a series to form a closed loop each nor gate in a first open condition, directing the flow of said product gas to an outlet port of said gate and, in a second closed condition, blocking the flow of said product gas and coupling the outlet port of said gate to a vent port of said gate, means for coupling the outlet port of each gate to the control port of the subsequent gate to form said closed loop thereby causing the gates to sequentially open and close such that each subsequent gate assumes an open or closed condition opposite to the condition of the preceding gate, the pneumatic pressure means at said outlet port for causing the subsequent gate to go to either an open or closed condition, a corresponding plurality of molecular sieve beds each pneumatically connected to the control port of said nor gates to adsorb said particular gas from said product gas, in said first open condition attenuate the rate of pressure rise in said control ports, and in said second closed condition attenuate the rate of pressure decay in said control port, and means for inferring the particular gas concentration of said product gas from the oscillation frequency of the monitor.

3. The monitoring system of claims 1 or 2, wherein said means for coupling comprises a restrictive orifice.

* * * * *